(12) United States Patent
Alvarez et al.

(10) Patent No.: US 11,877,898 B2
(45) Date of Patent: Jan. 23, 2024

(54) BIOPSY SITE MARKER

(71) Applicant: HOLOGIC, INC, Marlborough, MA (US)

(72) Inventors: Estefania Alvarez, Watertown, MA (US); Adam Kozak, Marlborough, MA (US); Jaimee Robertson, Marlborough, MA (US); Stephen Spiegelberg, Marlborough, MA (US)

(73) Assignee: HOLOGIC, INC., Marlborough, MA (US)

( * ) Notice: Subject to any disclaimer, the term of this patent is extended or adjusted under 35 U.S.C. 154(b) by 742 days.

(21) Appl. No.: 16/463,023

(22) PCT Filed: Sep. 27, 2017

(86) PCT No.: PCT/US2017/053782
§ 371 (c)(1),
(2) Date: May 22, 2019

(87) PCT Pub. No.: WO2018/097891
PCT Pub. Date: May 31, 2018

(65) Prior Publication Data
US 2019/0282325 A1    Sep. 19, 2019

Related U.S. Application Data

(60) Provisional application No. 62/425,953, filed on Nov. 23, 2016.

(51) Int. Cl.
*A61B 90/00* (2016.01)
*A61B 17/00* (2006.01)
*A61B 10/00* (2006.01)

(52) U.S. Cl.
CPC .......... *A61B 90/39* (2016.02); *A61B 10/0041* (2013.01); *A61B 2017/00796* (2013.01);
(Continued)

(58) Field of Classification Search
CPC ...................................................... A61B 90/39
See application file for complete search history.

(56) References Cited

U.S. PATENT DOCUMENTS

| 4,863,470 A | 9/1989 | Carter |
| 5,645,558 A | 7/1997 | Horton |

(Continued)

FOREIGN PATENT DOCUMENTS

| EP | 1125553 | 8/2001 |
| EP | 1579878 A1 | 9/2005 |

(Continued)

OTHER PUBLICATIONS

"HydroMARK Breast Biopsy Marker", Long-Term Ultrasound Visibility; https://www2.mammotome.com/hydromark-breast-marker?, © 2019 Devicor Medical Products, Inc., 4 pages.
(Continued)

*Primary Examiner* — Angela M Hoffa
*Assistant Examiner* — Younhee Choi
(74) *Attorney, Agent, or Firm* — JONES ROBB, PLLC

(57) ABSTRACT

A biopsy site marker configured to expand upon deployment into a biopsy cavity, and visible under several different imaging modalities, comprises a superabsorbent hydrogel component and a radiopaque element. The hydrogel is in a compressed, dehydrated state prior to deployment to facilitate placement of the marker within the biopsy site, and thereafter expands upon deployment in the biopsy site. Such expansion limits migration of the site marker.

28 Claims, 7 Drawing Sheets

(52) U.S. Cl.
CPC ............. *A61B 2017/00845* (2013.01); *A61B 2017/00853* (2013.01); *A61B 2017/00867* (2013.01); *A61B 2017/00898* (2013.01); *A61B 2090/3904* (2016.02); *A61B 2090/3908* (2016.02); *A61B 2090/3925* (2016.02); *A61B 2090/3954* (2016.02); *A61B 2090/3966* (2016.02); *A61B 2090/3987* (2016.02); *A61B 2090/3995* (2016.02)

(56) References Cited

U.S. PATENT DOCUMENTS

| | | |
|---|---|---|
| 5,766,219 A | 6/1998 | Horton |
| 6,090,125 A | 7/2000 | Horton |
| 6,254,633 B1 | 7/2001 | Pinchuk et al. |
| 6,356,782 B1 | 3/2002 | Sirimanne et al. |
| 6,371,904 B1 | 4/2002 | Sirimanne et al. |
| 6,428,558 B1 | 8/2002 | Jones et al. |
| 6,635,069 B1 | 10/2003 | Teoh et al. |
| 6,638,291 B1 | 10/2003 | Ferrera et al. |
| 6,725,083 B1 | 4/2004 | Burbank et al. |
| 6,766,186 B1 | 7/2004 | Hoyns et al. |
| 6,860,893 B2 | 3/2005 | Wallace et al. |
| 6,929,654 B2 | 8/2005 | Teoh et al. |
| 7,424,320 B2 | 9/2008 | Chesbrough et al. |
| 7,565,191 B2 | 7/2009 | Burbank et al. |
| 7,637,948 B2 | 12/2009 | Corbitt, Jr. |
| 7,668,582 B2 | 2/2010 | Sirimanne et al. |
| 8,060,183 B2 | 11/2011 | Leopold et al. |
| 8,112,869 B2 | 2/2012 | Jenks et al. |
| 8,224,424 B2 | 7/2012 | Burbank et al. |
| 8,280,486 B2 | 10/2012 | Miller et al. |
| 8,306,602 B2 | 11/2012 | Sirimanne et al. |
| 8,311,610 B2 | 11/2012 | Ranpura |
| 8,320,993 B2 | 11/2012 | Sirimanne et al. |
| 8,320,994 B2 | 11/2012 | Sirimanne et al. |
| 8,442,623 B2 | 5/2013 | Nicoson et al. |
| 8,480,706 B2 | 7/2013 | Chanduszko et al. |
| 8,600,481 B2 | 12/2013 | Sirimanne et al. |
| 8,718,745 B2 | 5/2014 | Burbank et al. |
| 8,747,597 B2 | 6/2014 | Rosqueta et al. |
| 9,095,342 B2 | 8/2015 | Becking et al. |
| 9,149,263 B2 | 10/2015 | Chanduszko |
| 9,216,069 B2 | 12/2015 | Foerster et al. |
| 9,271,736 B2 | 3/2016 | Heipl |
| 9,301,723 B2* | 4/2016 | Brannan ............ A61B 18/1815 |
| 9,380,998 B2 | 7/2016 | Sirimanne et al. |
| D767,138 S | 9/2016 | Apostolidis |
| 9,492,570 B2 | 11/2016 | Sirimanne et al. |
| 9,526,648 B2 | 12/2016 | Sharma |
| 9,585,669 B2 | 3/2017 | Becking et al. |
| 9,669,113 B1 | 6/2017 | Sirimanne et al. |
| 9,861,346 B2 | 1/2018 | Callaghan |
| 9,986,974 B2 | 6/2018 | Sirimanne et al. |
| 10,156,030 B2 | 12/2018 | Koppe |
| 10,413,381 B2 | 9/2019 | Hermann et al. |
| 10,463,376 B2 | 11/2019 | Bodewadt et al. |
| 10,500,014 B2 | 12/2019 | Hermann et al. |
| 10,709,453 B2 | 7/2020 | Suzuki |
| 10,808,341 B2 | 10/2020 | Koppe |
| 2005/0049489 A1 | 3/2005 | Foerster et al. |
| 2005/0090899 A1* | 4/2005 | DiPoto ............... A61B 17/7037 623/17.11 |
| 2006/0079805 A1 | 4/2006 | Miller et al. |
| 2007/0106361 A1* | 5/2007 | Epstein ................. A61L 31/048 623/1.1 |
| 2007/0135826 A1 | 6/2007 | Zaver et al. |
| 2008/0097190 A1 | 4/2008 | Hornscheidt et al. |
| 2008/0234532 A1* | 9/2008 | De Langen ............ A61B 90/39 600/8 |
| 2008/0269603 A1 | 10/2008 | Nicoson |
| 2009/0000629 A1 | 1/2009 | Hornscheidt et al. |
| 2009/0280182 A1* | 11/2009 | Beck .................... A61L 15/225 424/486 |
| 2010/0063458 A1 | 3/2010 | Barr |
| 2010/0234726 A1 | 9/2010 | Sirimanne et al. |
| 2013/0018259 A1 | 1/2013 | Borillo et al. |
| 2013/0066195 A1 | 3/2013 | Sirimanne et al. |
| 2013/0123830 A1 | 5/2013 | Becking et al. |
| 2013/0211495 A1* | 8/2013 | Halden ............ A61B 17/12109 623/1.12 |
| 2013/0289389 A1 | 10/2013 | Hermann et al. |
| 2014/0018663 A1 | 1/2014 | Harmer et al. |
| 2014/0051996 A1 | 2/2014 | Sirimanne et al. |
| 2014/0236014 A1 | 8/2014 | Swann |
| 2014/0243675 A1 | 8/2014 | Burbank et al. |
| 2014/0349367 A1* | 11/2014 | Jabbari ..................... C08J 3/075 435/182 |
| 2014/0371778 A1 | 12/2014 | Rudakov et al. |
| 2015/0005804 A1 | 1/2015 | Franano et al. |
| 2015/0007827 A1 | 1/2015 | Ozdil et al. |
| 2015/0238197 A1 | 8/2015 | Quinn et al. |
| 2016/0074023 A1 | 3/2016 | Sakamoto et al. |
| 2016/0106870 A1* | 4/2016 | Han .................... A61K 49/0404 424/9.411 |
| 2016/0206323 A1 | 7/2016 | Hebert et al. |
| 2016/0213380 A1 | 7/2016 | O'Brien et al. |
| 2016/0302924 A1* | 10/2016 | Boutillette ............ A61M 25/09 |
| 2016/0346453 A1 | 12/2016 | McGuckin, Jr. et al. |
| 2017/0086852 A1 | 3/2017 | Martinez et al. |
| 2017/0086854 A1 | 3/2017 | Cragg et al. |
| 2017/0156733 A1 | 6/2017 | Becking et al. |
| 2017/0245864 A1 | 8/2017 | Franano et al. |
| 2017/0367710 A1 | 12/2017 | Yang |
| 2018/0206851 A1 | 7/2018 | Walzman |
| 2018/0344425 A1 | 12/2018 | Burbank et al. |
| 2019/0021810 A1 | 1/2019 | He et al. |
| 2019/0076212 A1 | 3/2019 | Liu |
| 2019/0175184 A1 | 6/2019 | Hui et al. |
| 2019/0201160 A1* | 7/2019 | Hornscheidt .......... A61B 90/39 |
| 2019/0262002 A1 | 8/2019 | Benjamin |
| 2019/0282325 A1 | 9/2019 | Alvarez et al. |
| 2019/0314034 A1 | 10/2019 | Cragg et al. |
| 2020/0054413 A1 | 2/2020 | Vogel |
| 2020/0113647 A1 | 4/2020 | Hermann et al. |
| 2020/0163659 A1 | 5/2020 | Cahill |
| 2020/0340154 A1 | 10/2020 | Koppe |
| 2020/0367904 A1 | 11/2020 | Becking et al. |
| 2021/0022765 A1 | 1/2021 | Walzman |

FOREIGN PATENT DOCUMENTS

| | | |
|---|---|---|
| EP | 1782745 | 5/2007 |
| JP | 2005312941 | 11/2005 |
| JP | 2008143896 | 6/2008 |
| JP | 2015510437 | 4/2015 |
| JP | 2015524689 | 8/2015 |
| WO | 2006000568 | 1/2006 |
| WO | 2014013235 | 1/2014 |
| WO | 2014153267 A1 | 3/2014 |
| WO | 2014168750 A1 | 10/2014 |
| WO | 2014169261 A1 | 10/2014 |
| WO | 2017051248 A1 | 3/2017 |
| WO | 2017162126 A1 | 9/2017 |
| WO | 2017207777 | 12/2017 |
| WO | WO 2018/097891 A1 | 5/2018 |
| WO | 2019118374 A1 | 6/2019 |
| WO | 2020243474 A1 | 12/2020 |
| WO | 2021105506 | 6/2021 |
| WO | 2021105511 | 6/2021 |

OTHER PUBLICATIONS

JP Office Action dated Jul. 30, 2021 for JP Application No. 2019-527285, 14 pages.

International Search Report and Written Opinion of the International Searching Authority dated Dec. 12, 2017 for PCT/US2017/053782, 17 pages.

S.K. De et al: "Equilibrium swelling and kinetics of pH-responsive hydrogels: models, experiments, and simulations", Journal of Microelectromechanical Systems, vol. 11, No. 5, Oct. 1, 2002 (Oct. 1, 2002), pp. 544-555.

(56) References Cited

OTHER PUBLICATIONS

Office Action dated Mar. 29, 2022 for Japanese Patent Application No. 2019-527285, 11 pages.

* cited by examiner

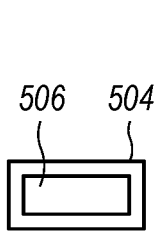
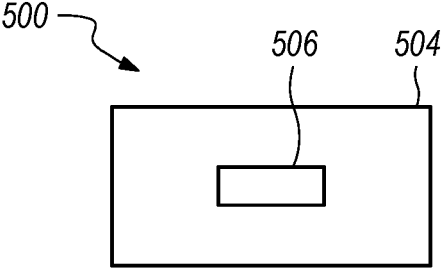
FIG. 5A
FIG. 5B
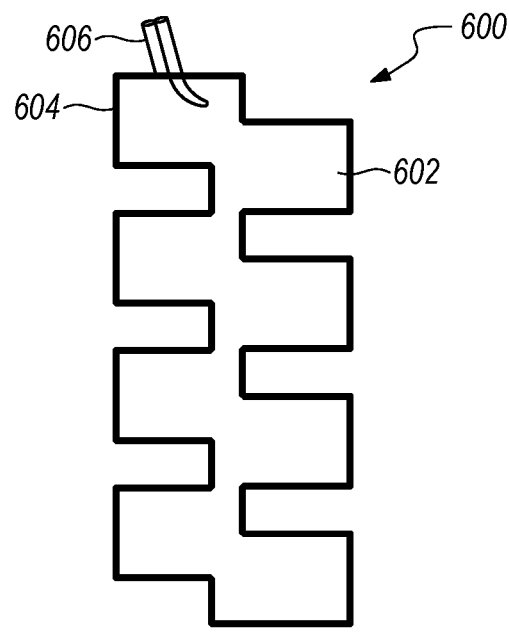
FIG. 6

BIOPSY SITE MARKER

RELATED APPLICATIONS DATA

The present application is a National Phase entry under 35 U.S.C § 371 of International Patent Application No. PCT/US2017/053782, having an international filing date of Sep. 27, 2017, which claims the benefit under 35 U.S.C. § 119 to U.S. Provisional Patent Application Ser. No. 62/425,953, filed Nov. 23, 2016, which is incorporated by reference in its entirety into the present application.

FIELD OF INVENTION

The disclosed inventions relate generally to site markers for breast biopsy procedures. More specifically, the disclosed inventions relate to site markers that are visible under several different imaging modalities.

BACKGROUND

In the diagnosis and treatment of breast cancer, it is often necessary to perform a biopsy to remove tissue samples from a suspicious mass. The suspicious mass is typically discovered during a preliminary examination involving visual examination, palpation, x-ray, magnetic resonance imaging (MRI), ultrasound imaging or other detection means.

When a suspicious mass is detected, a sample is taken by biopsy, and then tested to determine whether the mass is malignant or benign. This biopsy procedure can be performed by an open surgical technique, or through the use of a specialized biopsy instrument. To minimize surgical intrusion, a small specialized instrument such as a biopsy needle is inserted in the breast while the position of the needle is monitored using an imaging technique such as fluoroscopy, ultrasonic imaging, x-rays, MRI or other suitable imaging techniques.

In one biopsy procedure, referred to as stereotactic needle biopsy, the patient lies on a special biopsy table with her breast compressed between the plates of a mammography apparatus and two separate X-rays are taken from two different points of reference. A computer then calculates the exact position of the mass or lesion within the breast. The coordinates of the lesion are then programmed into a mechanical stereotactic apparatus which advances the biopsy needle into the lesion with precision. At least five biopsy samples are usually taken from locations around the lesion and one from the center of the lesion.

Regardless of the method or instrument used to perform the biopsy, subsequent examination of the surgical site may be necessary, either in a follow up examination or for treatment of a cancerous lesion. Treatment often includes a mastectomy, lumpectomy, radiation therapy, or chemotherapy procedure that requires the surgeon or radiologist to direct surgical or radiation treatment to the precise location of the lesion. Because this treatment might extend over days or weeks after the biopsy procedure, by which time the original features of the tissue may have been removed or altered by the biopsy, it is desirable to insert a site marker into the surgical cavity to serve as a landmark for future identification of the location of the lesion.

Known biopsy site markers have been found to have disadvantages in that the site markers are not visible under all available imaging modalities. Moreover, because of this problem, when cancer is found at a biopsy site that has been previously marked with a site marker, due to the poor visibility of the biopsy site marker under ultrasound or other visualization modalities, or lack of differentiation between marker and anatomical features, the patient must undergo an additional procedure that places an additional device within the biopsy site to enable the surgeon to find the biopsy site during surgery. Limited visibility (or none at all when using ultrasound) limits the ability to monitor tumor progression or shrinkage during neo adjuvant chemotherapy with the marker serving as a reference point. One known technique has been to place a breast lesion localization wire at the biopsy site. The localization wire is typically placed at the biopsy site via mammography and/or ultrasound.

Another issue that arises with site markers is migration. When the site markers are typically deployed to the biopsy site, the breast is still under compression. However, when the breast is released from compression, the site marker may migrate within the site or even out of the site through a needle tract created by the biopsy device, thereby preventing a surgeon or radiologist from easily locating the precise location of the lesion or biopsied area.

Accordingly, there is a need for site markers made from biocompatible materials that are visible under various modes of imaging to reduce the number of procedures that patients must undergo in detection and treatment of cancer. There is also a need to limit migration of a site marker when the site marker is placed in a biopsy site.

SUMMARY

In accordance with the disclosed inventions and embodiments thereof, a remotely detectable marker is provided for implantation in a targeted site within a patient's body from which tissue has been removed, wherein the marker comprises a radiopaque element having a distinguishing pattern for unique identification under x-ray imaging, and a non-palpable body coupled to the radiopaque marker. In one embodiment, the body is comprised of a substantially dehydrated material in a pre-deployment configuration, wherein the body is configured to expand between 5 and 100 percent greater than its pre-deployment volume in approximately 30 to 60 minutes when exposed to fluid, and to remain substantially physically stable when implanted within the targeted site for at least approximately 52 weeks, wherein the body is configured to reflect ultrasound in a way that the body is recognizable as being artificial and is distinguishable from the radiopaque marker. In one embodiment, the body is comprised of a substantially dehydrated material in a pre-deployment configuration, wherein the body has a swell ratio of 100-1000 wt/wt when exposed to fluid for approximately 30 to 60 minutes, and is configured to remain substantially physically stable when implanted within the targeted site for at least approximately 52 weeks, wherein the body is configured to reflect ultrasound in a way that the body is recognizable as being artificial and is distinguishable from the radiopaque marker.

In various embodiments, the radiopaque element (which may be metallic or polymeric) is be formed out of a braided, woven or mesh structure defining an interior region, wherein the body is contained within the interior region of the radiopaque element. In some embodiments, the radiopaque element is made out of PMMA or ultra-high molecular weight polyethylene (UHMWPE) compounded with a radiopacifier. In one such embodiment, the radiopaque element comprises PMMA that is loaded with approximately 30% to approximately 70%, and more preferably approximately 60%, barium sulfate by weight. In another embodiment, the radiopaque element comprises PMMA that is loaded with approximately 17% to approximately 23%, and preferably approximately 20%, bismuth trioxide by weight. In various embodiments, the PMMA is configured to achieve similar radiographic contrast as PEKK at a smaller volume than PEKK.

In various embodiments, the body of the marker is made out of a hydrogel, preferably configured to minimize a specular appearance under ultrasound when hydrated. In one such embodiment, the radiopaque element comprises PMMA, wherein the PMMA and hydrogel are configured to form covalent crosslinks. In one such embodiment, the body comprises one or more of pHEMA, PVP, PEGDA and PVA.

In various embodiments, the radiopaque element is formed by braided Nitinol tubing. In various embodiments, the radiopaque element is made from a shape memory material and/or a superelastic material. In one embodiment, the radiopaque element is made from a radiopacifier-loaded fiber. In one embodiment, the body of the marker comprises a first layer fixedly coupled to a second layer, the first and second layers each having a proximal end, wherein the respective proximal ends of the first and second layers are substantially aligned, the first layer comprising a thermoplastic and the second layer comprising of a substantially dehydrated material that swells upon contact with fluid to cause the second layer to transition to a post-deployment configuration, the post-deployment configuration having a distinguishing pattern. In such embodiment, the radiopaque element may be disposed proximal to the respective proximal ends of the first and second layers. In such embodiment, the second layer may be made out of shape memory thermoplastic.

In various embodiments, the body of the marker comprises a superabsorbent polymer contained in a polymer mesh. By way of non-limiting example, the body may be a folded or rolled polymer pouch containing the radiopaque element, wherein the pouch comprises a woven nylon mesh formed out of polyester thread filled with PVG/PEGDA granules. Alternatively, the radiopaque element may comprise PMMA or UHMWPE. In one embodiment, the pouch comprises a radiopaque fiber comprised of approximately 20 percent by weight bismuth trioxide.

Other and further aspects and features of the disclosed inventions will be evident from reading the following detailed description of the preferred embodiments, which are intended to illustrate, not limit, the invention.

BRIEF DESCRIPTION OF THE DRAWINGS

The drawings illustrate the design and utility of the disclosed embodiments, in which similar elements are referred to by common reference numerals. In order to better appreciate how the above-recited and other advantages and objects of the disclosed embodiments are obtained, a more particular description is set forth by reference to the accompanying drawings. Understanding that these drawings depict exemplary embodiments of the disclosed inventions, and are not therefore to be considered limiting, the illustrated embodiments will be described and explained with additional specificity and detail through the use of the accompanying drawings in which:

FIGS. 5A and 5B are plan views of a site marker in a dehydrated state and a hydrated state, respectively, according to a fourth embodiment;

FIG. 6 is a plan view of a site marker according to a fifth embodiment;

DETAILED DESCRIPTION OF THE ILLUSTRATED EMBODIMENTS

Biopsy markers are described herein for use in breast biopsy, but could be used in other areas. The markers described herein present a significant performance change from existing technologies without substantially adding to the cost of this fundamentally high volume product. Existing products provide an unacceptably short duration of ultrasound contrast and have been prone to migration from the original biopsy location due to a lack of tissue adhesion to cavity walls, mechanical attachment, or rapid expansion upon deployment. These deficiencies suggest a new device comprised of a hydrogel, or similar technology, surrounding a radiopaque core or a hydrogel contained within a flexible envelope.

Preferably, a biopsy site marker provides permanent radiographic contrast and distinct ultrasound contrast for a minimum of one year (fifty-two weeks) within limited posterior acoustic shadowing. The portion of the marker providing ultrasound contrast may be either permanent or biodegradable. The marker preferably has a "man-made" shape to clearly differentiate it from other biological structure and abnormal features. The permanent portion of the marker preferably sits in the middle of the cavity. The marker is preferably configured to minimize migration and improve tissue adhesion relative to existing cavity structure. The marker preferably swells to fill the biopsy cavity, yet not swell so much that it is palpable by the patient. Delivery of the marker is preferably single-handed and as simple as possible. The shelf life is preferably at least two years.

Figure 1:
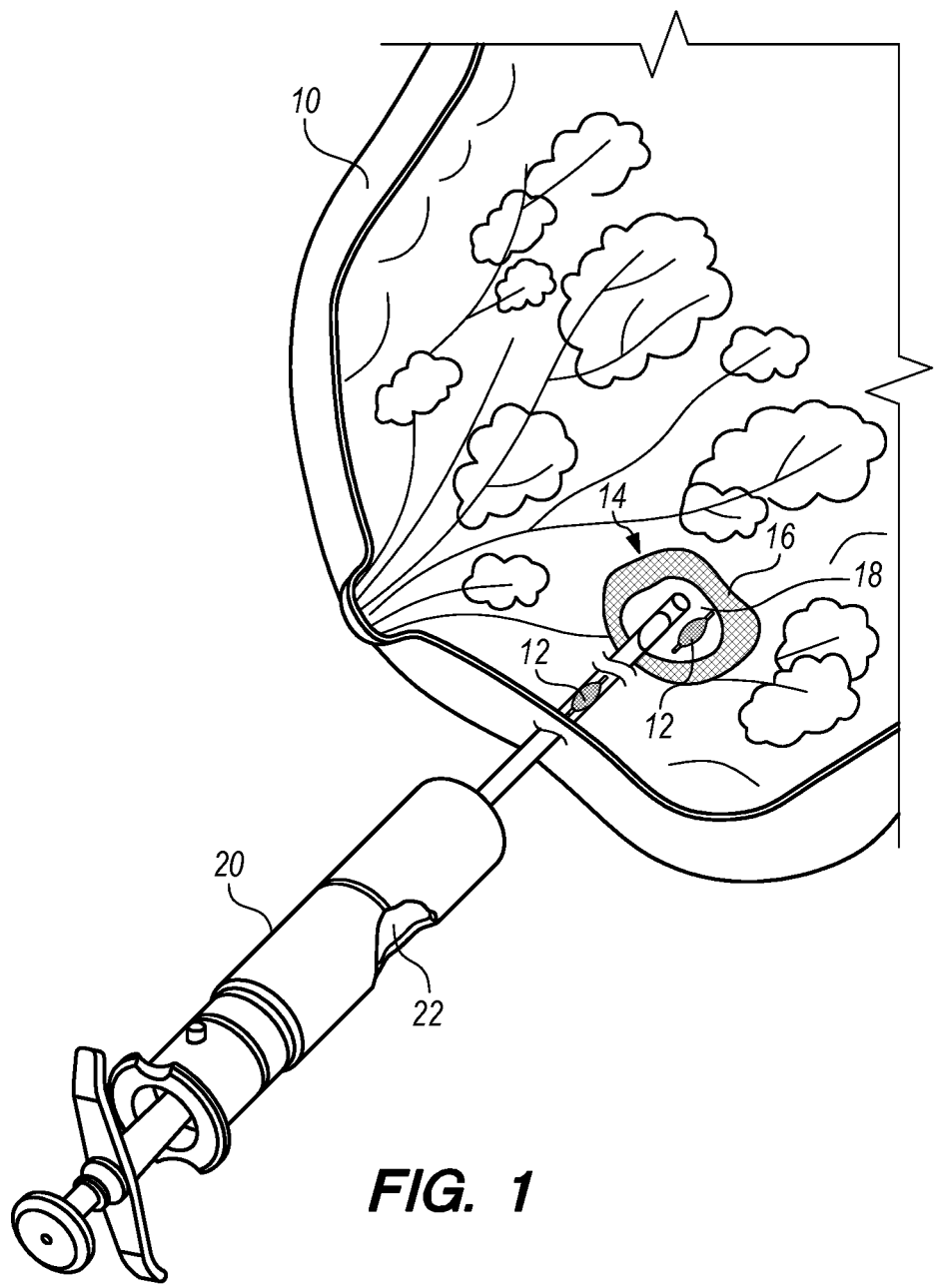
FIG. 1 is a perspective view of a biopsy site in a human breast showing the breast in section and one or more site markers being implanted in the biopsy cavity.

FIG. 1 illustrates a perspective view of a human breast 10 being implanted with a site marker 12 according an embodiment of the disclosure. At a biopsy site 14 is a lesion 16 from which a tissue sample has been removed, resulting in a biopsy cavity 18. One or more site markers 12 are implanted in the biopsy cavity 18 using a marker delivery system 20. In one embodiment, the marker delivery system 20 advanced by sliding it through an inner lumen 22 of a biopsy device (not shown), which avoids the need to withdraw the biopsy device and thereafter insert the marker delivery system 20. Delivering the site marker 12 in the biopsy cavity 18 without withdrawing the biopsy device reduces the amount of tissue damage and enables more accurate placement of the site marker 12. The marker delivery system 20 illustrated in FIG. 1 is exemplary only and it is understood that the site marker embodiments disclosed herein are suitable for use with other marker delivery systems.

FIGS. 2A-5B illustrate various exemplary site marker embodiments according to the present disclosure. In general, the site markers described herein are made from biocompatible materials that have appropriate densities for radiographic imaging, appropriate surface characteristics, and acoustic impedance differences for ultrasonic imaging, and appropriate magnetic characteristics for magnetic resonance imaging. The constituent materials of the site markers are either not biodegradable or can be tuned to degrade over a long time scale. The fifty-two week scale encompasses a typical timespan in which a physician would need visibility of the marker to be able to monitor a full round of neo adjuvant chemo therapy, in order to reduce the tumor significantly leading to lumpectomy. In particular, uniformity of acoustic impedance in the marker is highly desirable. A strong impedance mismatch will result in a clear outline using ultrasound, and the ability of the hydrogels described herein to maintain a constant impedance throughout yields a "clean" and speckle-free image, whereas a hydrogel with heterogenous impedance would yield a speckled image, and may be mistaken for tissue, which is further discussed below.

The site markers disclosed herein in the pre-deployment state are solid compacted structures, in dehydrated states reduced in size from their desired final state. These markers also have a distinct 3D configuration in a hydrated state. Upon deployment in a biopsy cavity, the markers are configured to expand in situ immediately and reach full size within thirty to sixty minutes. The markers may expand axially (in height) and longitudinally (in width) to a size that is larger than the initial size of the biopsy tract. Preferably, the fully expanded marker occupies more than 50% of the diameter of the biopsy cavity. This expansion can be tailored based on the type of polymer used for the superabsorbent hydrogel, the conditions under which the polymer has been prepared (e.g., different processing conditions which may influence e.g. crosslink density and affect swell ratio/swell kinetics), the surface area of the polymer, swelling rate of the polymer, the give or elasticity of a polymer/metal envelope that contains the hydrogel polymer, the processing conditions to set the final/expanded shape and its final dimensions, the amount of saline used for deployment, and the amount of bodily fluids within the biopsy cavity. This tailored expansion could aid in precise marking of the lesion and precise deployment, and preventing the marker from being displaced within the biopsy cavity or biopsy track. The time frame of sixty minutes allows a radiologist to confirm placement after deployment using any imaging modality, and to confirm placement with a mammogram shortly after the marker is deployed. In particular, the markers will start to become visible under U/S and MRI within minutes, and will reach their "final" deployed state within an hour of being deployed in the patient's body This is routine practice as radiologists image at deployment and confirm with a mammogram before a patient leaves the facility. A fully expanded marker preferably has a non-palpable feel at deployment, and in the long term due to the selection of biocompatible materials should trigger a minor tissue inflammatory response with minimal scar formation.

Figure 2A:
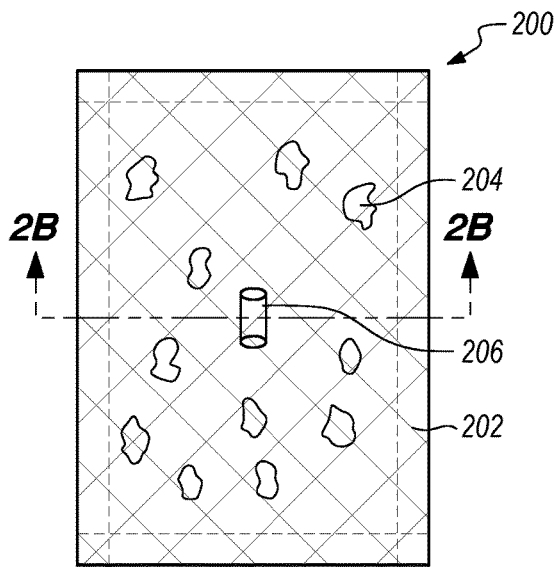
FIGS. 2A and 2C are plan views of a site marker according to a first embodiment.
Figure 2C:
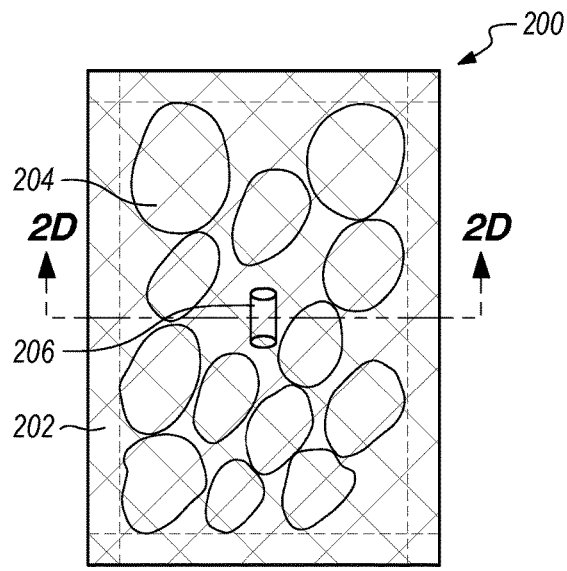
Figure 2B:
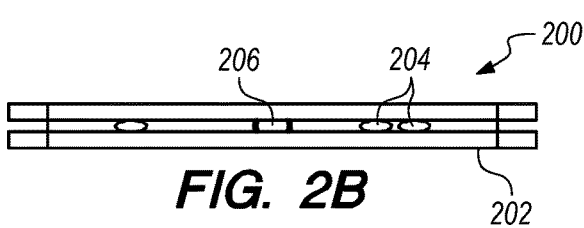
FIGS. 2B and 2D are cross-sectional views along lines 2B-2B and 2D-2D in FIGS. 2A and 2C, respectively.

In one embodiment, shown in FIGS. 2A-2D, a gel mesh biopsy marker 200 includes a polymer mesh pouch or envelope 202, superabsorbent hydrogel granules 204 disposed within the pouch 202, and a radiopaque element 206 disposed within the pouch 202. Prior to deployment in a biopsy cavity, the gel granules 204 are in a dehydrated state and the mesh pouch 202 is relatively flat, as shown in FIGS. 2A and 2B. When the granules 204 are dehydrated, the gel mesh biopsy marker 200 may be rolled or folded for delivery into the biopsy cavity. Upon deployment into the biopsy cavity, the pouch 202 immediately unrolls or unfolds to lie flat. This unrolling, or unfolding, increases the width of the marker 200, making it unlikely that the marker 200 can migrate along the biopsy cavity.

Figure 2D:
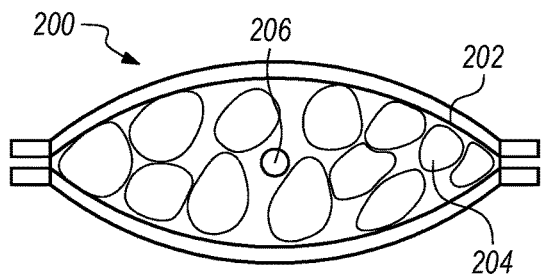

Upon delivery to the biopsy cavity, the hydrogel granules 204 absorb liquid. For example, the marker deployment process may include a saline wash to accelerate hydration of the granules 204, wherein the saline wash is intended to accelerate the hydration/expansion and allow for a more predictable deployment behavior (i.e. more predictable hydration kinetics, time from deployment to first visibility under U/S or MRI). But even without the saline wash, the hydrogel component will absorb physiological fluids (blood, interstitial fluid), as further discussed herein. During the liquid absorption, the granules 204 swell to expand and fill the pouch 202, as shown in FIGS. 2C and 2D. Depending on the conditions of the deployment, the gel mesh marker 200 may expand fully within approximately 10 minutes. The expansion is limited by the hydrogel loading, hydrogel chemistry and the dimensions, give or elasticity the mesh pouch 202. The surface area and elasticity of the mesh pouch 202 defines the maximum possible displacement, while the quantity of gel granules 204 within the pouch 202 defines the actual displacement and the stiffness of the fully swollen marker 200. Marker expansion therefore occurs by two mechanisms—mesh pouch unfolding/unrolling and water absorption by the gel granules 204.

The mesh pouch 202 may be made of a polymer, such as nylon. The mesh pouch 202 may be a woven nylon mesh sewn, by way of non-limiting example, into a rectangular patch geometry using polyester thread. Other patch geometries are also possible, and the patch may also be assembled via techniques other than sewing, such as by ultrasonic or thermal welding The mesh is a fine mesh that prevents the granules 204 from escaping through the holes in the mesh in either the dry or hydrated state. In other words, the openings in the mesh are significantly smaller than the granules 204. Further, the hydrogel granules in the hydrated state are sufficiently rigid (i.e., have a high enough modulus or physical integrity) to prevent being "squeezed" out through the pores under physiological loads expected within the biopsy cavity.

The granules 204 may be superabsorbent hydrogel granules. For example, the granules 204 may be made of a co-polymer of polyvinylpyrrolidone and poly(ethylene glycol) diacrylate (PVP/PEGDA) that provides ultrasound and MRI contrast. In one embodiment, the hydrogel granules are a PVP/PEGDA gel prepared with the following formulation: 15% vinyl pyrrolidone, 7.5% poly(ethylene glycol) dimethacrylate (700 g/mol), and 1% sodium chloride in water. Relative to the monomer content, 1% 2,2-dimethoxy-2-phenylactophenone may be added as a photoinitiator to enable crosslinking via ultraviolet radiation. The resulting formulation may be UV cured in a polystyrene petri dish for approximately 20 minutes (e.g., with a light source of approximately 48 W, and approximately 254 nm). After this time, the gel may be swollen in distilled water overnight to remove unreacted products, then dried at 80° C. for approximately 8 hours to remove the water. The gel may then be ground using a grinder and the resulting material may be sieved to yield granules 204 of approximately 50-100 μm in size, which are loaded into the polymer mesh pouch 202 prior to closure with the polyester thread.

The radiopaque element 206 may comprise a poly(methyl methacrylate) (PMMA) shape loaded with radiopacifier. The PMMA can easily be formed into unique shapes via molding or die extrusion, for example. Such a unique shape would allow for easy identification under x-ray imaging. Material radiopacity and density of PMMA in the current configuration limits or eliminates the traditional black artifact that surrounds metal based markers when visualized under mammography and tomosynthesis. These artifacts could lead to a misrepresentation of an anatomical feature surrounding the marker. Thus PMMA allows easier identification of the marker permanently without limiting surround anatomy or lesion of interest. In one embodiment, the radiopaque element 206 used in the gel mesh marker 200 is a cylindrical PMMA marker approximately 400 μm in diameter. For example, KYPHON HV-R bone cement powder and liquid components, modified to yield a 60% wt/wt barium sulfate concentration, may be mixed for approximately sixty seconds and then extruded through a 22 gauge needle onto a polyethylene surface and cut into approximately 3 mm long sections. These radiopaque elements 206 may be loaded into the mesh pouch 202 together with the hydrogel granules 204.

Figure 2E:
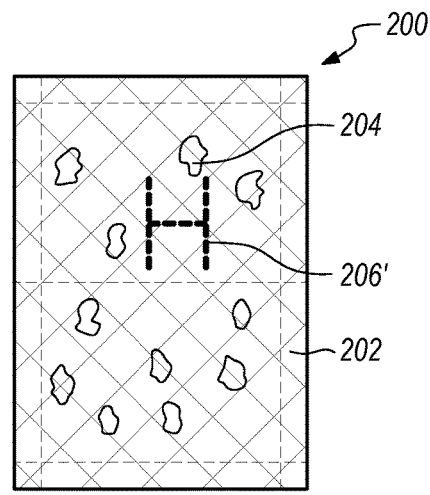
FIG. 2E is a plan view of an alternate embodiment to FIGS. 2A-2D.

In another embodiment, the radiopaque element may be attached to the pouch 202 rather than contained within the pouch 202. For example, as shown in FIG. 2E, a radiopaque thread 206' embroidered into the mesh pouch 202 serves as the radiopaque element. Alternatively or additionally, the radiopaque thread 206' could be used to design a custom mesh that incorporates the thread 206' into the mesh itself in identifiable patterns. For example, the radiopaque thread 206' may be a radiopaque fiber (e.g., Dyneema Purity® (DSM)) incorporated into the gel mesh marker 200' to provide contrast when viewed using x-ray imaging. The radiopaque fiber 206' may be a medical grade ultra-high molecular weight polyethylene (UHMWPE) loaded with approximately 20% bismuth trioxide by weight. Embroidery of the fiber 206' into the mesh 202, or incorporating the fiber as part of the mesh, ensures attachment of the fiber 206' to the mesh 202 and allows patterning for unique identification.

The gel mesh marker 200 has been shown to be visible under several different imaging modalities. During ultrasound imaging, the water content of the hydrogel component 204 provides a hypoechoic region, distinctly outlined by hyperechoic polymer mesh 202. Some optimization of hydrogel loading may be required in order to ensure complete material hydration at equilibrium (partially hydrated hydrogel particles result in a "specular" appearance which reduces overall marker contrast). X-ray visibility is achieved by the inclusion of the radiopaque polymer element 206, 206' inside or on the surface of the polymer pouch 202. Under MRI imaging (wherein the mechanism for the MRI contrast is the high relative water content of the hydrogel relative to surrounding tissue), the hydrogel 204 contained within the gel mesh marker 200 appears as a bright shape (signal enhancement) in the T2 weighted image sequence and as a dark shape under T1 weighted image sequences. Alternatively, it may be desirable to create a specular appearance with distinct 'big bubbles' or other types of artifacts that remain permanently visible, e.g., like a signature, to make it easier to differentiate as a man-made structure.

Figures 3A, 3B:
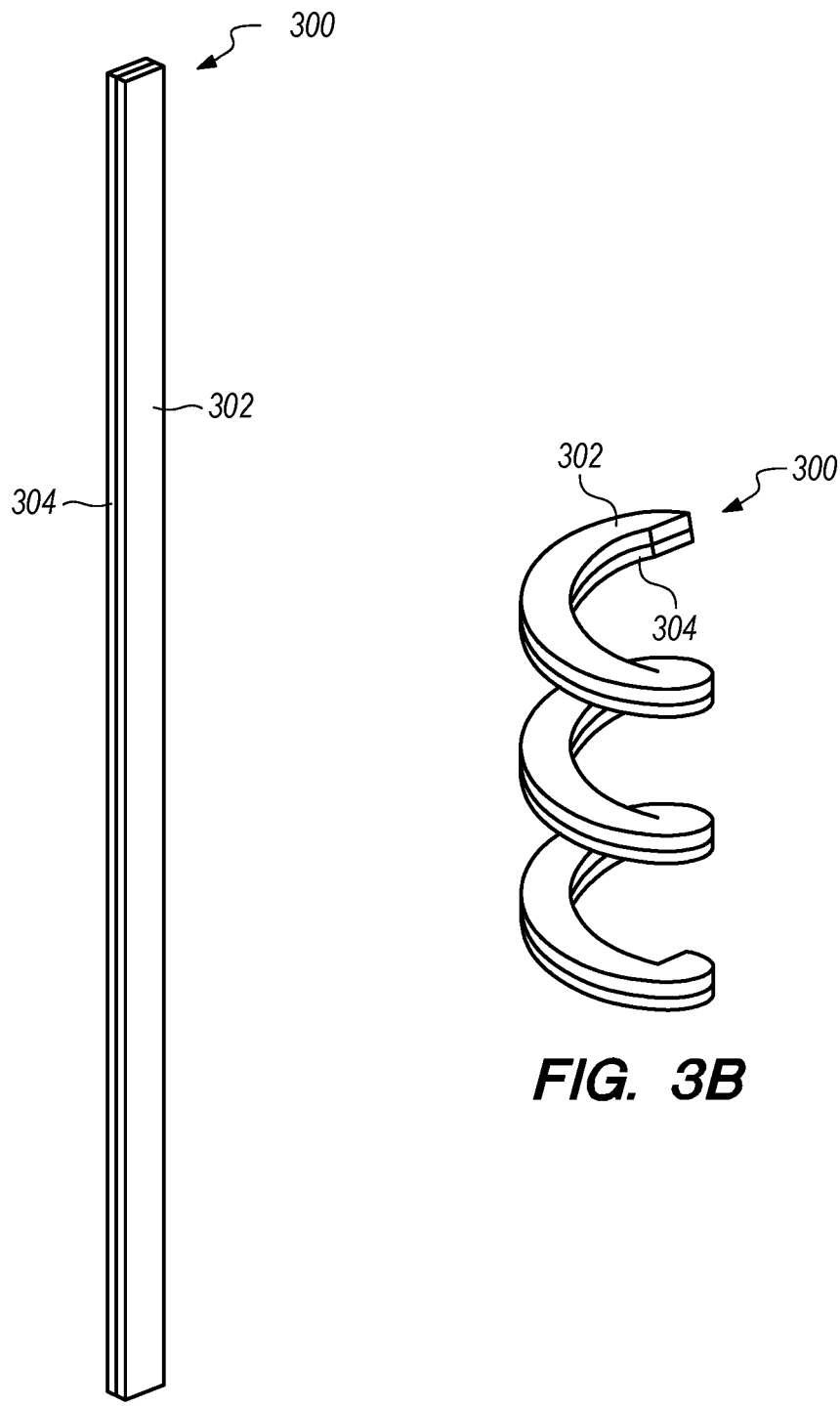
FIGS. 3A and 3B are perspective views of a site marker according to a second embodiment in a dehydrated state, and a hydrated state, respectively.

In another embodiment, shown in FIGS. 3A-3D, a biopsy marker 300 comprises a bilayer composite material that resembles a curly fry in the hydrated state, which is shown in FIG. 3B. The curly fry biopsy marker 300 starts off as a flat strip (FIG. 3A) comprising a superabsorbent hydrogel layer 302 in a dehydrated state and a mesh layer imbibed with hydrogel 304, forming a continuous gel network through the thickness of the biopsy marker 300. Upon hydration, the superabsorbent hydrogel layer 302 swells to a higher degree than the mesh layer 304, although the mesh 304 does not swell to any significant degree. In particular, the mesh 304 constricts the hydrogel swelling, and is deformed by the hydrogel in a manner that is dependent on the mesh properties (e.g. anisotropy in extensibility, pore geometry) and the mechanical properties of the hydrogel. The nonhomogeneous expansion results in curling to a helical geometry. The high swell ratio of the hydrogel layer 302 enables space-filling expansion and (under some modalities) imaging contrast. The curly fry biopsy marker 300 may be delivered into the biopsy cavity, deploying in response to hydration. Alternatively or additionally, the marker 300 may be placed in a cannula for delivery and expelled using a push rod to deploy. A backflush with saline or water may be used to ensure a rapid rate of swelling.

The initial marker 300 may be rectangular in shape with approximate dimensions of 3 cm length×0.1 cm width×0.05 cm thickness. As the hydrogel 302 absorbs water and swells, the biopsy marker 300 curls, forming a helical geometry, aka, "curly fry" shape. This curly fry shape change is diffusion limited, and is triggered once the bulk hydrogel softens. The curling may begin within 3-5 minutes after exposure to water, and the final geometry may be attained in approximately 30 minutes. More rapid shape change may be achieved by deploying the marker 300 in the hydrated or partially hydrated state, or by adjusting the hydrogel formulation. The final size of the marker 300 is approximately 1.0 cm length×0.5 cm diameter. Thus, the overall length of the marker 300 decreases upon hydration, but the effective diameter increases significantly. The swelling and resulting diameter growth may fill the biopsy cavity and localize the marker 300 to the biopsy site.

As such, in addition to hydrogel expansion, the curly fry marker 300 incorporates a shape transforming mechanism to assist in filling the biopsy cavity and in preventing migration. In particular, the curly fry marker 300 transforms from essentially a 2D strip to a 3D (curled) structure. The final 3D helix, which is only achieved upon hydration of the gel 302, assists in preventing the migration of the marker 300 from the biopsy site. Each ring or curl within the helix is substantially aligned concentrically making it stay within a cylinder like structure. However, depending of the mesh orientation, configuration, and processing of the bulk hydrogel, or by having different blocks of hydrogel chemistries embedded in the mesh), individual rings or curls of the helix may be offset from the central axis, creating a "discontinuous" curly fry structure with protruding rings/curls that function somewhat like a threaded screw to aid in keeping the marker confined at the site of implantation. In particular, the 3D helix hydrogel geometry can be adjusted through control of the mesh and hydrogel properties. For example, positioning blocks of hydrogels with different chemistries along the length of the biopsy marker could lead to variable curvature in the deployed state. In such a case, the diameter of the helix could vary along the length or reach a maximum in the center of the marker. Similar diameter variation could be obtained through control of the relative thickness of the hydrogel and imbibed mesh layers. For instance, with a constant hydrogel layer thickness, a thicker mesh layer would have a larger curled diameter due to increased stiffness and resistance to curling. Variation of the mesh orientation along the length of the biopsy marker could lead to a variable pitch along the length of the curled 3D helix. Further, adding additional structural features to the mesh (e.g. creasing, folding, thermal welds), may allow a change of the angle of the central axis of the helix.

Figure 3C:
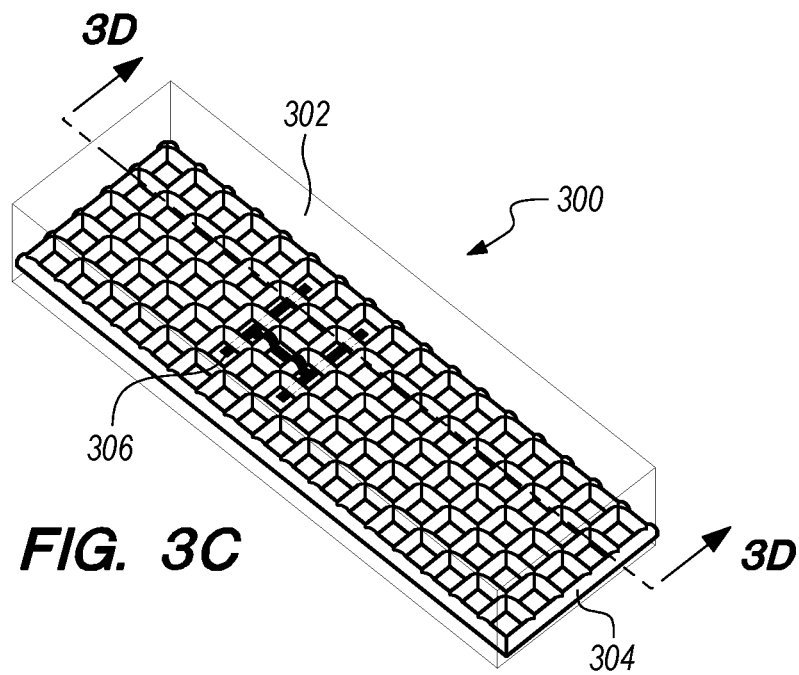
FIG. 3C is an enlarged view of a portion of the second embodiment in the dehydrated state.
Figure 3D:
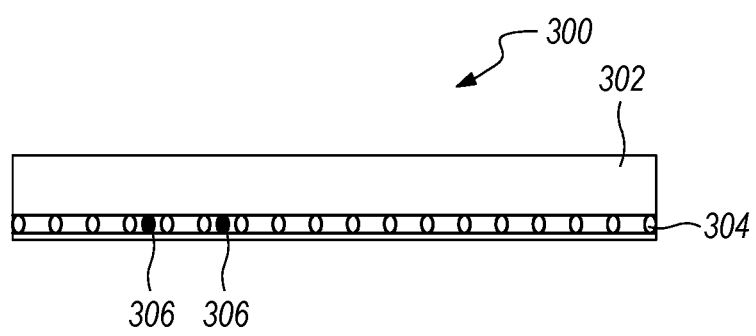
FIG. 3D is a cross-sectional view of the second embodiment along line 3D-3D in FIG. 3C.

A limitation of a bilayer design can be the adhesion between plies. As the curly fry marker 300 relies on non-homogeneous swelling, inherent stresses at the boundary between layers 302 and 304 in the curled marker may cause delamination at the interface between the non-swelling and swelling layers. The mesh 304 may alleviate this issue, as the hydrogel precursor infiltrates the mesh 304, as shown in FIGS. 3C and 3D, allowing more continuity of the hydrogel 302 through the thickness of the marker 300. With excess hydrogel 302 on one surface, the composite becomes a bilayer structure with a hydrogel layer 302 and a layer of mesh 304 embedded in hydrogel 302. Such interpenetration of the hydrogel 302 may allow for good adhesion between the layers 302 and 304, limiting delamination effects.

In order to obtain pitch in the curling of the bilayer marker 300, the mesh 304 may be formed of a material that elastically deforms in an anisotropic manner. Specifically, the mesh 304 may stretch more in one direction than in the perpendicular direction. The relative difference in stretch between the two directions, along with the orientation of the mesh 304 in the marker 300, dictates the final geometry of the curled biopsy marker 300. A mesh without this anisotropy may enable curling, but with zero pitch.

In one embodiment, the curly fry marker 300 incorporates a radiopaque element in the form of a thread 306 that is embroidered into the mesh 304. Alternatively or additionally, the radiopaque thread 306 may be used to design a custom mesh that incorporates the thread in identifiable patterns.

The curly fry marker 300 preferably includes a hydrogel component 302 that has a high swell ratio and is tough, deformable, and resistant to crack propagation. To achieve these properties, a poly(vinyl pyrrolidone-co-ethylene glycol dimethacrylate)/poly(vinyl alcohol) blend (PVPEGDA/PVA) may be used as the hydrogel 302. PVPEGDA alone has a high swell ratio, but is highly notch sensitive. Such a property is not ideal for the curly fry marker 300, as the boundaries between the mesh 304 and the gel 302 can serve as sites for crack initiation. PVA is a hydrogel known for its toughness, though alone, may be too stiff for the curly fry marker 300, and the swelling is not completely reversible. Combined, the PVPEGDA/PVA is more resistant to crack propagation and can be reversibly swelled in water or saline.

The PVPEGDA/PVA gel may be prepared with the following formulation: 15% vinyl pyrrolidone, 5% poly(ethylene glycol) dimethacrylate (700 g/mol), 5% poly(vinyl alcohol) (106,000-110,000 g/mol, 99.3+super hydrolyzed), and 1% sodium chloride in water. Relative to the monomer content, 1% 2,2-dimethoxy-2-phenylactophenone may be added as a photoinitiator to enable crosslinking via ultraviolet radiation.

The mesh layer 304 may be a polyester mesh with a negligible swell response in water. Polyesters are widely used in medical applications and typically, are not biodegradable. For example, when considering long term contrast created by the mesh, the mesh layer 304 may comprise poly(ethylene terephthalate), or PET, which is used frequently in biomedical materials, in particular sutures, tendon reconstruction, vascular grafts, and surgical meshes, and PET is resistant to biological degradation, so the mechanical properties and imaging contrast may be stable for more than a year. Notably, long term contrast created by the hydrogel will be dependent on the stability of the hydrogel.

The radiopaque element 306 used in the curly fry marker 300 may be a radiopaque fiber similar to the fiber 206' described above with respect to the gel mesh marker 200. The fiber 306 may be attached to the mesh 304 prior to imbibing in the hydrogel 302 to ensure attachment to the marker 300. The mesh 304 with the attached radiopaque fiber 306 may be imbibed with the PVPEGDA/PVA hydrogel 302 to form the biopsy marker 300.

The curly fry biopsy marker 300 has been shown to be visible under several different imaging modalities. While the water content in the hydrogel 302 is expected to provide strong ultrasound contrast, the resulting signal under this imaging modality is complex. Due to the three dimensional folded structure of the bilayer marker 300, the resulting signal may show a clear hypoechoic border around the hyperechoic mesh 304 but overall appearing as a discontinuous shape with some posterior acoustic shadowing. Exemplary x-ray contrast was provided via the radiopaque UHMWPE fiber 306 attached to the mesh component 304. The water content of the hydrogel component 302 provided excellent MRI contrast, appearing as a bright white region in the T2 weighted scans and as a dark shape under T1 and fat suppression image sequences.

Figure 4A:
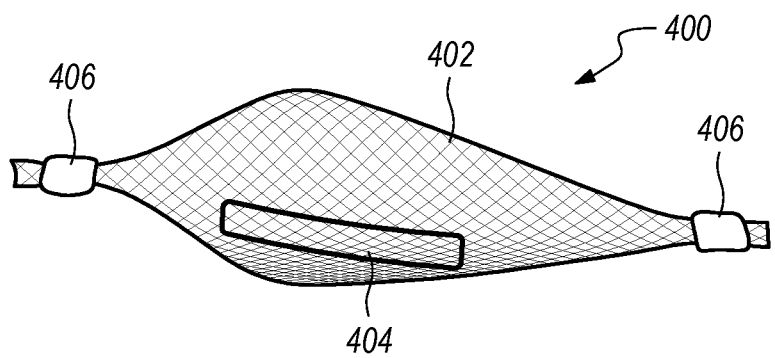
FIGS. 4A and 4B are perspective views of a site marker in an expanded state and a contracted state, respectively, according to a third embodiment.
Figure 4B:
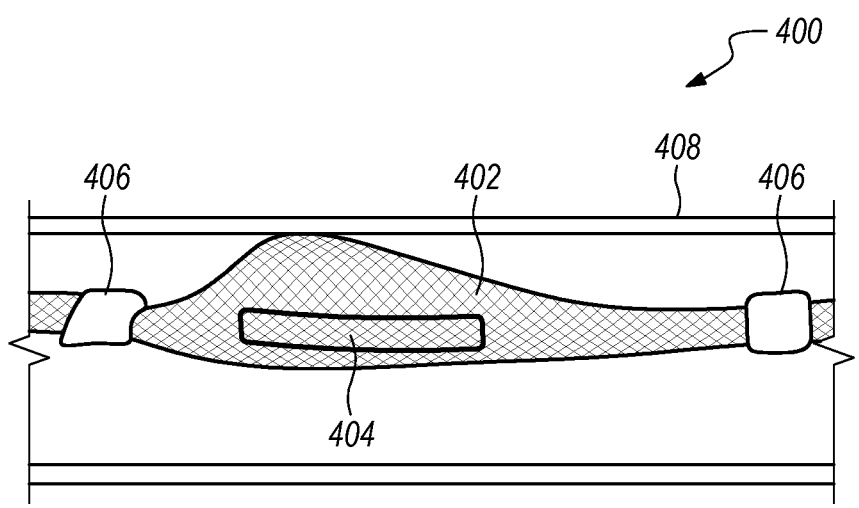

In another embodiment, shown in FIGS. 4A and 4B, a shape memory-based biopsy marker 400 comprises a cage 402 surrounding a superabsorbent hydrogel core 404. The cage 402 may have a torpedo-like or teardrop-like shape, and comprises a superelastic shape memory material. For example, the cage 402 may be made of Nitinol. The marker 400 further includes crimp beads 406 at either end of the cage 402. The crimp beads 406 may be metallic, or alternatively made of a polymer, and are used to close off the respective ends of the Nitinol cage 402, thereby enclosing the hydrogel component 404 within the cage 402 to provide unique X-ray identification. It will be appreciated that other means may be employed to close off the ends of the cage 402, such as welding or knotting, the latter of which may for example be realized by a drawstring and cinch mechanism. After the hydrogel core 404 is positioned within the cage 402, the ends of the cage 402 may be closed off with the crimp beads 406. In some embodiments, the crimp beads 406 are metallic, and may comprise titanium, gold, silver, or the like. In one example, the Nitinol cage 402 may be radially compressed and threaded through a 0.8 mm silver plated brass crimp bead 406. In such embodiments, the metallic composition of the crimp bead 406 may provide further radiographic contrast with minimal to no MRI artifacts. Alternatively, the cage 402 may be constructed using Nitinol having a shape transition temperature approximately the same as body temperature, and flushing with warm/hot saline to trigger a thermal transition, i.e. thereby relying on the true shape memory mechanism, rather than rely on superelasticity.

Nitinol is the preferable shape memory material for the cage 402 due to its robust shape memory properties and the ability to tune the activating temperature through composition. In one example, the cage-like structure 402 is made of braided Nitinol tubing. The braiding technique may impart desirable properties in the 3D tubing construct. Specifically, the Nitinol tubing is highly compressible through radial compression and highly expandable through axial compression. After release of either the radial or axial compressive force, the Nitinol tubing elastically contracts to its native state. The extreme diameter changes result from the braided geometry. Properties such as the maximum outer diameter, the braid density, and the elastic response of the tubing can be adjusted through the braiding parameters.

The superelasticity of the Nitinol may be utilized as a means for compact delivery in a small diameter cannula and rapid space filling upon deployment in the biopsy cavity. The Nitinol cage 402 may be set to a permanent expanded shape with a desired tapering diameter and a desired length. For example, the diameter of the cage 402 may be approximately 0.5 cm at the maximum point, and the length of the cage 402 may be approximately 1.0 cm. The shape memory marker 400 may be compressed to a smaller diameter such that the Nitinol tubing forming the cage 402 are in contact with the hydrogel core 404. In this form, the shape memory marker 400 is easily inserted into a cannula 408 for deployment, as shown in FIG. 4B. The size of the cannula 408 is therefore likely limited by the diameter of the hydrogel component 404, although the profile of the crimp beads 406 or alternative cage sealing material, as well as the diameter of the Nitinol tubing/wire forming the braid may also limit cannula size. The shape memory marker 400 may be extruded into the biopsy cavity using a simple push rod, and may be back flushed with saline to accelerate swelling of the hydrogel 404. Upon exiting the cannula 408, immediate elastic expansion assists in precise marking of lesion, localizing the marker 400 and preventing migration from the biopsy site. In addition, the torpedo-like shape may help prevent migration of the marker 400 along the biopsy tract during retraction of the cannula 408. As a larger diameter in the distal portion of the marker, prevents marker migration in the direction of least resistance such as the biopsy tract.

The hydrogel core 404 in the shape memory marker 400 provides ultrasound and MRI contrast. The hydrogel core 404 may, for example, be approximately 0.5 cm long and 0.8 mm in diameter in the dehydrated state. In one embodiment, the hydrogel 404 is a poly(vinyl pyrrolidone-co-ethylene glycol dimethacrylate) (PVPEGDA) gel prepared with the following formulation: 7.5% vinyl pyrrolidone, 2.5% poly (ethylene glycol) dimethyacrylate (700 g/mol), and 1% sodium chloride in water. Relative to the monomer content, 1% 2,2-dimethoxy-2-phenylactophenone may be added as a photoinitiator to enable crosslinking via ultraviolet radiation. The resulting formulation may be cast in quartz tubing (e.g., 2.3 mm nominal ID) to obtain cylindrical hydrogel rods. Lower overall monomer content was used for the hydrogel component 404 of the shape memory marker 400 compared to the hydrogels used in the other marker embodiments. The lower monomer content allows for a higher swell ratio, but reduces the mechanical strength of the gel in the swollen state. The shape memory marker design encapsulates the hydrogel 404 within a cage structure 402, and thus, does not rely on mechanical strength of the hydrogel 404 during potential marker removal.

The shape memory marker 400 is distinct from the other marker embodiments in that no radiopaque element was added solely for the purpose of imaging contrast. In some embodiments, the Nitinol cage 402 and the crimp beads 406 are metallic and inherently radiopaque. Adjustment of the permanent shape of the Nitinol cage 402 or the size, shape, or number of the crimp beads 406 may enable differentiation between multiple biopsy sites.

The shape memory marker 400 (including the crimp beads 406) may be coated with a thin hydrogel layer (e.g., polyethylene glycol (PEG) or the like) or other low friction materials (e.g. ePTFE, silicone, poly(glycerol sebacate) PGS) that may aid in reducing friction of the shape memory marker 400 upon deployment. Such a coating may facilitate deployment of the shape memory marker 400 out of the distal end of a delivery device, and may also prevent shredding of the cage 402 due to friction between the outer surface of the cage 402 and the inner surface of a delivery cannula. This coating may also provide another enhancement for ultrasound visualization. Alternate deployment strategies (e.g. using a soluble plug—discussed below) may also prevent damage to the marker during deployment.

The shape memory marker 400 has been shown to be visible under several different imaging modalities. For example, ultrasound imaging of the shape memory marker 400 demonstrated distinct echogenic contrast between the hyperechoic Nitinol edge and hypoechoic hydrogel interior. The resulting effect is a dark interior shape with a bright "outline" when viewed in cross-section. The Nitinol wire configuration is easily visualized as a thin hyperechoic crisscrossed structure with a hypoechoic background when the ultrasound transducer is scanned of the marker. The crimp beads 406 (which may be composed of silver plated brass, for example) on either end of the cage 402 also provide distinct hyperechoic contrast. The fully deployed shape memory biopsy marker 400 is visible under x-ray, which clearly captures the Nitinol wire in the braided shape of the cage 402 as well as the crimp beads 406 on either side of the marker 400. Due to the thin wire diameter, the marker 400 does not mask tissue behind the marker 400 and surrounding media, and as such the marker 400 appears translucent (a.k.a, a "mesh screen" effect). Both the Nitinol and hydrogel components are identifiable using MRI. The Nitinol cage 402 appears as a dark outline around the bright hydrogel core 404 in T2 weighted images. In T1 weighted images, the entire marker 400 appears as a dark region.

In yet another embodiment, shown in FIGS. 5A and 5B, a swelling bead biopsy marker 500 comprises a solid radiopaque core 506 coated with a superabsorbent polymer hydrogel 504. The swelling bead marker 500 is delivered to the biopsy cavity with the hydrogel 504 in a dehydrated state, and the hydrogel 504 expands upon delivery into the biopsy cavity. Marker deployment may include a saline wash to accelerate hydration of the hydrogel 504.

In order to achieve x-ray contrast, the radiopaque core 506 may comprise a PMMA shape loaded with radiopacifier. The PMMA can easily be formed into unique shapes via molding or die extrusion, for example. For example, the radiopaque element 506 used in the swelling bead marker 500 may be a cylindrical PMMA marker approximately 400 µm in diameter prepared in the same manner as the radiopaque element 206 described above with respect to the gel mesh marker 200. The PMMA core 506 may be hard and rigid, while the hydrogel 504 may be soft and brittle. The compatibility of the PMMA chemistry with the hydrogel 504 may result in chemical bonds being formed between the hydrogel 504 and the PMMA core 506 during curing. In particular, if the hydrogel chemistry is chosen carefully and/or if the underlying radiopaque element has undergone appropriate surface treatment e.g. functionalization/silane modification of a metallic radiopaque marker, then covalent chemical bonding may occur during polymerization of the hydrogel material, occurring between the hydrogel material and the radiopaque element, improving adhesion between these two dissimilar materials.

The hydrogel component 504 in the swelling bead marker 500 provides ultrasound and MRI contrast. In one embodiment, the hydrogel 504 is a PVP/PEGDA gel prepared with the following formulation: 15% vinyl pyrrolidone, 7.5% poly(ethylene glycol) dimethyacrylate (700 g/mol), and 1% sodium chloride in water. Relative to the monomer content, 1% 2,2-dimethoxy-2-phenylactophenone may be added as a photoinitiator to enable crosslinking via ultraviolet radiation. The resulting formulation may be UV cured in a half filled 2 mm diameter cylindrical quartz mold sealed with parafilm for approximately sixty seconds (the light source may be, for example, approximately 48 W, and approximately 254 nm). Alternatively, a 1 mm diameter quartz mold may be employed for a smaller marker diameter. After this time, the radiopaque marker 506 (e.g., PMMA, 60% barium sulfate wt/wt) may be loaded into the center of the hydrogel and the remainder of the quartz mold may be filled with gel precursor solution. The resulting gel may be UV cured for an additional 15 minutes. The gel may be extruded from the quartz mold and swollen in distilled water to remove unreacted products, then dried at 80° C. to remove the water prior to loading into a delivery device. This multi-step curing process specifically allows for the radiopaque element to be positioned and correctly oriented in the center of the surrounding hydrogel.

The swelling bead marker 500 has been shown to be visible under several different imaging modalities. During ultrasound imaging, the swelling bead marker 500 is hypoechoic with a clear, sharp boundary around the marker 500, with hyperechoic radiopaque element 506 located inside. X-ray visibility is achieved by the inclusion of the radiopaque element 506. Under MRI, the marker 500 appears as a bright shape in a T2 weighted image sequence and as a dark shape under T1 and fat suppression image sequences. The smooth edges of the swelling bead marker 500 clearly distinguish the marker 500 as man-made.

In another embodiment, shown in FIG. 6, a biopsy marker 600 comprises a foam material 602, a sticky coating 604, and a radiopaque element 606. Prior to deployment, the foam marker 600 comprises compressed, pre-shaped foam 602. As shown in FIG. 6, the foam 602 has a zig zag pattern to allow for the marker to be folded down for loading into the delivery device and subsequent expansion/unfolding upon delivery, but it should be readily understood that any shape may be used. The compressibility of the foam 602 allows for deployment in a reduced size state, and upon deployment the foam 602 may expand, unfold and fill in the biopsy cavity. The foam 602 may preferably be saturated with fluid upon deployment, so as to retain more fluid, thereby reducing air content and shadowing. Alternatively or additionally, the foam 602 may be pre-soaked with fluid and then deployed.

The foam 602 may be an open cell foam (e.g., silicone elastomer) or a closed cell foam (e.g., polyethylene and/or silicone, textured silicone, etc.). In one example, the foam 602 is a closed cell polyester, meaning that the polymer structure will contain entrapped air that will increase ultrasound contrast due to impedance mismatch, MRI contrast due to lack of signal from within the foam cells, and overall signal permanence due to a lack of tissue ingrowth.

The foam 602 may be coated with a sticky coating 604 (e.g., a low molecular weight PEG, mucoadhesive hydrogel such as a thiolated PVA hydrogel, or the like) to aid in adhesion to the cavity walls, which may reduce migration. Although FIG. 6 depicts the coating 604 outlining the foam 602, it should be readily understood that the coating 604 covers the entire outer surface of the foam 602. In one embodiment, the foam 602 is dip-coated in a low molecular weight PEG (e.g., 2000 g/mol), which is solid at room temperature and body temperature but tacky due to the sub ambient glass transition temperature of the material. The foam 602 may undergo a single coating process in a solution of 30% PEG in isopropyl alcohol heated to 80° C.

The radiopaque element 606 may be (without limitation) made of titanium, which has been used in FDA-cleared permanent implants. The titanium wire may be shaped into a unique form to further act as an identifier for the foam biopsy marker 600. Multiple shapes could be used to enable distinction between biopsy sites.

Figure 7A:
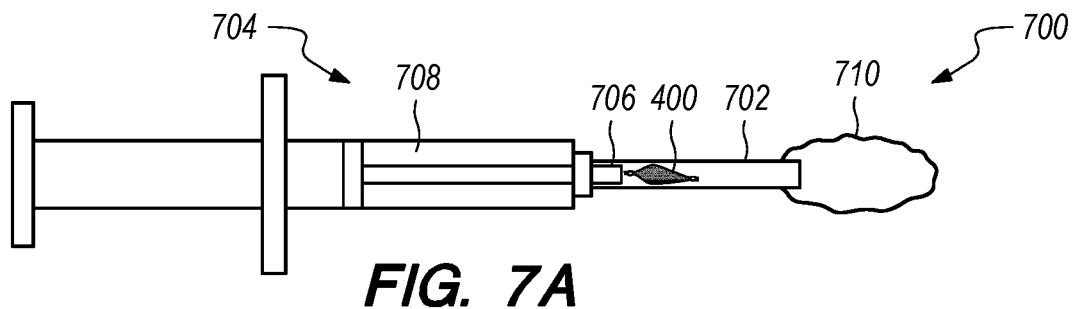
FIGS. 7A, 7B, and 7C are plan views of a delivery device prior to marker deployment and after marker deployment, respectively.
Figure 7B:
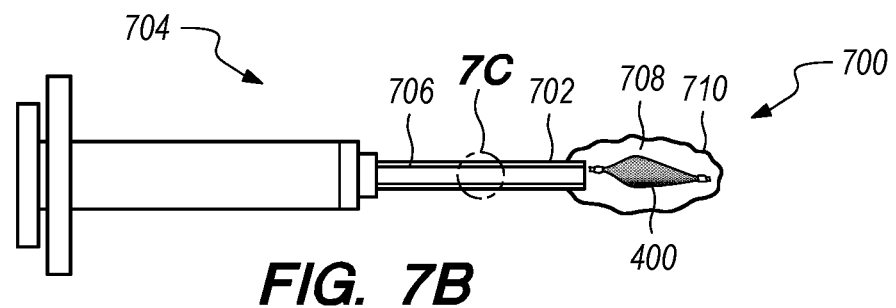
Figure 7C:
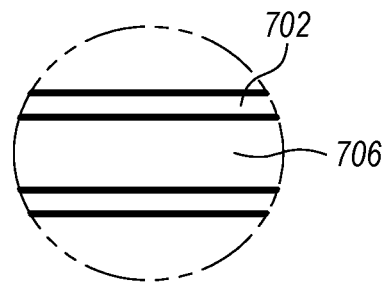

As shown in FIGS. 7A and 7B, the biopsy markers described above may be delivered by a delivery device 700 that comprises a cannula 702 with an attached syringe 704 for back flushing with saline 708 and a push rod 706 for deploying the markers. Although FIGS. 7A and 7B depict the shape memory marker 400 being deployed, it should be well understood that the delivery device 700 may be used to deliver any of the site markers described above. All of the marker embodiments include a hydrogel component that is designed to provide ultrasound contrast and to assist with migration prevention through swelling and filling a biopsy cavity 710. As such, rapid swelling is preferable for immediate ultrasound imaging capabilities and prevention of migration during delivery cannula 702 retraction. The addition of excess saline 708 upon marker deployment accelerates the swelling process and provides improved ultrasound contrast.

The delivery device 700 allows a one-step deployment that accomplishes delivery of the marker 400 as well as the addition of saline 708 to the biopsy site 710. The biopsy marker 400 may be pre-loaded in the delivery cannula 702, as shown in FIG. 7A. The syringe 704 with the attached push rod 706 may be filled with saline 708 to a desired volume and attached to the cannula 702 containing the marker. Such attachment may be a standard Leuer lock twist fit, or a custom attachment. After positioning the cannula 702 at the biopsy cavity 710, simply pushing the syringe plunger advances the push rod 706, which pushes the biopsy marker 400 into the cavity 610, as shown in FIG. 7B. Simultaneously, saline 708 can be delivered to the biopsy site 710. As shown in greater detail in FIG. 7B, the inner push rod 706 is sized such that the outer diameter is slightly smaller than the inner diameter of the cannula 702, which allows the flow of saline 708 between the push rod surface and the cannula 702.

Having separate cannulas and syringes may allow for sale of the individual components, further minimizing the cost of the marker. The marker could be sold within a disposable cannula, ready for deployment, and medical facilities could have one or more attachable syringe devices on hand.

Figure 8:
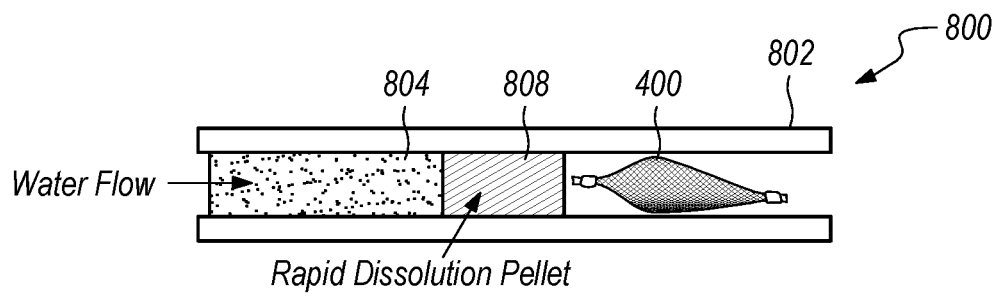
FIG. 8 is an alternate embodiment of a delivery device for the site markers.

In another embodiment, shown in FIG. 8, a delivery device 800 comprises a water soluble pellet 808 (e.g., composed of sucrose, PEG, or the like) rather than a push rod. The water soluble pellet 808 is positioned in a cannula 802 between the biopsy marker 400 and saline 804, and is forced forward by fluid pressure during depression of the syringe plunger (not shown). The plunger displaces the biopsy marker 400 into the biopsy cavity as well as the water soluble pellet 808, which will eventually dissolve. Once the water soluble pellet 808 is displaced into the biopsy cavity, the saline solution 804 is free to fill the cavity and contribute to hydration of the biopsy marker 400. An advantage of this embodiment is that the soluble pellet 808 distributes the force of the deployment and reduces possibility for damage to the biopsy marker.

Each of the embodiments described above with reference to FIGS. 2A-6 comprises a hydrogel for enhanced ultrasound and MRI contrast and for limiting marker migration. The expansion behavior post deployment serves to center the marker within the biopsy cavity and prevent migration. The hydrogel is castable/moldable which allows for the marker to be manufactured in a variety of shapes. The hydrogel may be loaded with other additives such as radiopacifiers and can potentially be bonded to underlying substrates depending on their surface chemistry.

The swelling kinetics of the hydrogel components differ between the gel mesh marker 200 and the other three marker embodiments due to the surface to volume ratio. The higher surface to volume ratio of the hydrogel granules 204 in the gel mesh marker 200 allows more rapid swelling to equilibrium. The swelling bead marker 500, curly fry marker 300, and shape memory marker 400, while slower at reaching the equilibrium swell state, will immediately absorb water and form a hydrated shell around a dehydrated core. As such, all markers described above should be visible under ultrasound and MRI shortly after deployment, but only the gel mesh marker 200 may be in its final state approximately 10 minutes after deployment. The other markers 300, 400, and 500 may require about an hour to reach full hydration.

The hydrogel may be composed of polyacrylamide. Polyacrylamide hydrogels commonly have swell ratios in the range of 100-1000 (wt/wt), and a 500-1000 μm dry bead may swell up to 1-2 cm in size depending on the nature of the aqueous solvent (e.g., pH, salt content). The mechanical properties of the polyacrylamide may be adjusted by tuning the crosslink density, resulting in a softer or more firm gel upon full hydration. Polyacrylamide is resistant to biological degradation, so the properties and imaging contrast should be stable for more than fifty-two weeks. The swelling kinetics of polyacrylamide will depend on the surface area to volume ratio of the material. As the surface area to volume ratio increases (which will be generally true for smaller markers), the time required to reach an equilibrium volume will decrease. The material used for the hydrogel may also be a combination of one or more of: poly(2-hydroxyethyl methacrylate) (pHEMA), polyvinylpyrrolidone (PVP), poly(ethylene glycol) diacrylate (PEGDA), poly(vinyl alcohol) (PVA). For example, the swelling bead marker 500, gel mesh marker 200, and shape memory marker 400 may employ a co-polymer of PVP/PEGDA, while the curly fry marker 300 may employ a co-polymer of PVP/PEGDA/PVA. It should be appreciated that material selection may affect reaction to biological fluids. Certain materials (e.g. polyacrylamide) will be sensitive to the ionic character of the surrounding fluid and will exhibit different swell ratios (and therefore imaging contrast by U/S and MRI) when exposed to blood vs interstitial fluid vs DI water. Selecting a material that is relatively insensitive to ionic character of the surrounding fluid (e.g. as the PVP/PEGDA and PVP/PEGDA/PVA) ensures a more predictable and consistent response during end use.

Once a material or materials are selected, many variables remain which will affect the functional performance of the hydrogel. The functional performance of the hydrogel material includes its ultrasound contrast, MRI contrast, swelling kinetics, swell ratio at equilibrium, mechanical properties (dry and swollen state), biocompatibility, degradability, processability, manufacturability, compatibility within the larger marker construct, and even radiopacity. These performance parameters are related to physical properties of the hydrogel such as the solid content, the crosslink density, and the molecular weight between crosslinks. In turn, these may be tuned by adjusting the hydrogel monomer content, relative ratio of monomers (in the case of a co-polymer), the molecular weight of the starting materials, the initiator content, the curing time/temperature/UV dose, or additives such as plasticizers or porogens. For example, with a PVP hydrogel prepared by direct UV crosslinking, the higher the molecular weight of the starting material, the greater the ultrasound contrast of the hydrogel. This is due to increased molecular weight between crosslinks, which allows for a looser polymer network to form, which allows for greater equilibrium water content.

The majority of commercially available biopsy markers employ a metallic component for radiographic contrast. These may be in the form of metal tubing, wires or coils, which present a limited number of shapes that may be obtained without complex manufacturing, or in the form of micro-machined shapes, which can be expensive to produce on a large scale. Use of a radiopacifier loaded polymer as the radiopaque element in the above-described embodiments may allow for such designs to be injection molded or extruded into a variety of shapes in a more cost-effective manner.

In one embodiment, the radiopaque polymer may be PMMA loaded with barium sulfate, specifically employing a modified formulation of commercially available bone cement, KYPHON HV-R, supplied by Medtronic. Modified formulations may be generated from the starting material by preparing bone cement samples with barium sulfate concentrations ranging from 30% (unmodified base material) to 70% by weight. As the barium sulfate concentration increases, the physical integrity of the final material decreases and the x-ray contrast of the PMMA formulations increases. At 70% wt/wt concentration of barium sulfate the PMMA is qualitatively observed to be brittle in nature. A 60% wt/wt concentration of barium sulfate may be preferable for preparation of radiopaque elements in the gel mesh marker 200 and the swelling bead marker 500. The PMMA marker loaded with 60% barium sulfate may achieve qualitatively similar radiographic contrast at a fraction of the size of a commercially available PEKK marker. This may allow for overall miniaturization of the PMMA marker and deployment through smaller gauge delivery devices.

A secondary benefit of the PMMA as a carrier material for the radiopacifier may be the presence of acrylate groups on the surface of the material. For the hydrogel systems studied here, which are partially formed by crosslinking which occurs at the acrylate end groups of the PEGDA chains, the acrylate groups on the surface of the PMMA radiopaque marker can react with the hydrogel and form covalent crosslinks, resulting in a strong bond between the two materials in the case of the swelling bead embodiment. Such a reaction would not be possible on many other surfaces (e.g., Nitinol, titanium) without complex surface modification.

In another embodiment, the radiopaque element may be a radiopacifier-loaded fiber. The advantage of this form is that for woven or braided constructs, such as the gel mesh, curly fry, or shape memory embodiments, a radiopaque polymer fiber may be incorporated into the larger marker in a patterned form to provide a unique radiographic shape for marker identification. The radiopacifier loaded fiber may be a Dyneema RP dtex 135 TS1000 UHMWPE fiber loaded with 17-23% bismuth trioxide by weight.

All of the markers are identifiable under three imaging modalities —ultrasound, x-ray, and MRI. Under ultrasound, the markers are similar in that the hydrogel component appears as a dark region due to the high water content. The gel mesh marker 200 appears different in that the mesh 202 appears as a hyperechoic outline around a thin layer of the hydrogel 204, though the thickness of the hydrogel 204 can be tuned by adjusting the geometry/elasticity of the mesh 202 or the swelling pressure of the hydrogel 204. The mesh form has a "candy wrapper" appearance. The swelling bead marker 500 appears as a hypoechoic cylinder surrounding the hyperechoic radiopaque element 506. The smooth surfaces of the swelling bead marker 500 give it a man-made appearance. The Nitinol cage 402 in the shape memory marker 400 appears as a hyperechoic outline around the hydrogel hypoechoic core 404, similar to the gel mesh marker 200. The Nitinol cage has a distinct ultrasound contrast (without any posterior acoustic shadowing) making it to be easily identified by either an expert radiologist and also for people with limited knowledge in this area. The curly fry marker 300 is more difficult to identify under ultrasound due to the complex structure, but in the proper position, a hypoechoic outline (hydrogel) can be seen around the hyperechoic mesh. Minor shadowing is observed for the gel mesh marker 200 and curly fry marker 300. All markers are located in x-ray images by bright white (x-ray absorbing) regions. The shape memory marker 400 is different from the other markers under x-ray, as the entire marker is viewed in the images. The Nitinol cage 402 appears distinct, with the crimp beads 406 showing as larger bright regions. The small diameter of the Nitinol tubing/wire, the Nitinol tubing/wire orientation, the picks per inch (or porosity of the Nitinol cage) prevent the contrast from masking tissue behind the shape memory marker permanently 400. The other markers only have a radiopaque element in the center or at one end of the marker, but still the contrast is sufficient for localizing the markers.

Under T2 weighted MRI images, the markers appear similar in that the hydrogel component appears as a bright region due to the high signal from the water content. The gel mesh marker 200 and shape memory marker 400 are slightly different, as they have dark regions/outlines surrounding the hydrogel due to the polyester mesh 202 and Nitinol cage 402. The curly fry marker 300 also appears unique due to the hollow core within the helical structure. The hydrogel appears bright, while the void space within the marker shows as a dark region. True "voids" may be gradually filled by tissue ingrowth after implantation, and this feature of the ultrasound contrast will gradually decrease in magnitude, ultimately disappearing. Under T1 weighted MRI images, the hydrogel components of the markers appear as dark shapes.

Although particular embodiments of the disclosed inventions have been shown and described, it will be understood that this is not intended to limit the disclosed inventions to the preferred embodiments, and it will be obvious to those skilled in the art that various changes and modifications may be made without departing from the scope of the present inventions, which are intended to cover alternatives, modifications, and equivalents of the disclosed embodiments, as defined by the claims.

What is claimed is:

1. A remotely detectable marker for implantation in a targeted site within a patient's body from which tissue has been removed, the marker comprising:
    a radiopaque element comprising a braided, woven or mesh structure formed by polymeric threads and defining an interior region and having a distinguishing pattern for unique identification under x-ray imaging, wherein, upon implantation in the targeted site, the radiopaque element is configured to transition from a collapsed shape to an expanded shape, the expanded shape being different than the collapsed shape; and
    a non-palpable body contained within the interior region of the radiopaque element, the non-palpable body being configured to transition between a pre-deployment configuration and a post-deployment configuration when exposed to a fluid, wherein:
        in the pre-deployment configuration, the non-palpable body comprises a substantially dehydrated material, and
        in the post-deployment configuration, the substantially dehydrated material of the non-palpable body swells to a final, fully expanded size, such that a post-deployment volume of the non-palpable body is between 5 and 100 percent greater than a pre-deployment volume of the non-palpable body in approximately 30 to 60 minutes, to partially fill a cavity at the targeted site, and to remain substantially physically stable when implanted within the cavity for at least approximately 52 weeks, the non-palpable body being configured to reflect ultrasound in a way that the non-palpable body is recognizable as being artificial and is distinguishable from the radiopaque element when implanted within the cavity, and
    wherein, in the post-deployment configuration, when the non-palpable body is in the final, fully expanded size, the non-palpable body fills less than an entirety of the interior region of the expanded shape of the radiopaque element.

2. The marker of claim 1, wherein the radiopaque element comprises polyethylene fibers.

3. The marker of claim 2, wherein the polyethylene fibers are formed from an ultra-high molecular weight polyethylene (UHMWPE) compounded with a radiopacifier.

4. The marker of claim 3, wherein the UHMWPE is loaded with about 17% to about 23% bismuth trioxide by weight.

5. The marker of claim 3, wherein the UHMWPE is loaded with about 20% bismuth trioxide by weight.

6. The marker of claim 1, wherein the non-palpable body is made out of a hydrogel.

7. The marker of claim 6, wherein the non-palpable body comprises one or more of poly(2-hydroxyethyl methacrylate) (pHEMA), Polyvinylpyrrolidone (PVP), poly (ethylene glycol) diacrylate (PEGDA), and Polyvinyl alcohol (PVA).

8. The marker of claim 1, wherein the radiopaque element includes a radiopacifier-loaded fiber.

9. The marker of claim 1, wherein the expanded shape of the radiopaque element is a torpedo-like or teardrop-like shape.

10. The marker of claim 1, wherein the expanded shape of the radiopaque element is different than a shape of the non-palpable body in the post-deployment configuration when the non-palpable body is in the final, fully expanded size.

11. The marker of claim 1, wherein a shape of the non-palpable body in the post-deployment configuration is a cylindrical shape.

12. The marker of claim 1, wherein the expanded shape of the radiopaque element comprises:
    a length extending between a first end of the radiopaque element and a second end of the radiopaque element; and
    a diameter that varies along the length, wherein a maximum diameter of the radiopaque element is located closer to the first end of the radiopaque element than the second end of the radiopaque element.

13. The marker of claim 12, wherein the length is about 1.0 cm, and the maximum diameter is about 0.5 cm.

14. The marker of claim 1, wherein a shape of the non-palpable body in the post-deployment configuration, when the non-palpable body is in the final, fully expanded size, is different than a shape of the interior region of the radiopaque element in the expanded shape of the radiopaque element.

15. The marker of claim 1, wherein the polymeric threads include radiopaque and polyester threads.

16. A remotely detectable marker for implantation in a targeted site within a patient's body from which tissue has been removed, the marker comprising:
a radiopaque element comprising a braided, woven or mesh structure formed by polymeric threads and defining an interior region, the radiopaque element being movable from a collapsed shape to an expanded shape and having a distinguishing pattern for unique identification under x-ray imaging; and
a non-palpable body disposed within the interior region of the radiopaque element, the non-palpable body comprising a substantially dehydrated material,
wherein, when exposed to a fluid during the implantation, the non-palpable body has a swell ratio of 100-1000 wt/wt for approximately 30 to 60 minutes, such that the non-palpable body has a final, fully swelled shape that is configured to partially fill a cavity at the targeted site and to remain substantially physically stable within the cavity for at least approximately 52 weeks,
wherein the final, fully swelled shape of the non-palpable body is different than the expanded shape of the radiopaque element, and
wherein the non-palpable body is configured to reflect ultrasound in a way that the non-palpable body is recognizable as being artificial and is distinguishable from the radiopaque element.

17. The marker of claim 16, wherein the non-palpable body has a nominal maximum swelling represented by a volumetric change of up to approximately 8000%.

18. The marker of claim 16, wherein the non-palpable body is made out of a hydrogel.

19. The marker of claim 16, wherein the non-palpable body comprises one or more of poly(2-hydroxyethyl methacrylate) (pHEMA), Polyvinylpyrrolidone (PVP), poly (ethylene glycol) diacrylate (PEGDA), and Polyvinyl alcohol (PVA).

20. The marker of claim 16, wherein the radiopaque element includes a radiopacifier-loaded fiber.

21. The marker of claim 16, wherein the expanded shape of the radiopaque element comprises:
a length extending between a first end of the radiopaque element and a second end of the radiopaque element; and
a diameter that varies along the length of the radiopaque element, wherein a maximum diameter of the radiopaque element is located closer to the first end of the radiopaque element than the second end of the radiopaque element.

22. The marker of claim 21, wherein the length is about 1.0 cm, and the maximum diameter is about 0.5 cm.

23. The marker of claim 16, wherein the final, fully swelled shape of the non-palpable body is different than a shape of the interior region of the radiopaque element.

24. The marker of claim 16, wherein the polymeric threads include radiopaque and polyester threads.

25. The marker of claim 16, wherein the radiopaque element comprises polyethylene fibers.

26. The marker of claim 25, wherein the polyethylene fibers are formed from an ultra-high molecular weight polyethylene (UHMWPE) compounded with a radiopacifier.

27. The marker of claim 26, wherein the UHMWPE is loaded with about 17% to about 23% bismuth trioxide by weight.

28. The marker of claim 26, wherein the UHMWPE is loaded with about 20% bismuth trioxide by weight.

* * * * *